United States Patent [19]

Jackson

[11] Patent Number: 5,174,284
[45] Date of Patent: Dec. 29, 1992

[54] ENDOSCOPIC BITE BLOCK

[75] Inventor: Frank W. Jackson, Mechanicsburg, Pa.

[73] Assignee: G.I. Supply, Inc., Camp Hill, Pa.

[21] Appl. No.: 755,404

[22] Filed: Sep. 5, 1991

[51] Int. Cl.⁵ .............................................. A61M 16/06
[52] U.S. Cl. ............................ 128/200.26; 128/200.24; 128/859
[58] Field of Search ................... 128/200.26, DIG. 26, 128/846, 848, 200.24, 857, 859, 860, 861; 602/902

[56] References Cited

U.S. PATENT DOCUMENTS

| D. 283,158 | 3/1986 | Jackson | D24/128 |
|---|---|---|---|
| 1,674,336 | 6/1928 | King | 128/848 |
| 2,693,182 | 11/1954 | Phillips | 128/208 |
| 2,820,457 | 1/1958 | Phillips | 128/351 |
| 2,857,911 | 11/1956 | Bennett | 128/147 |
| 2,908,269 | 10/1959 | Cheng | 128/12 |
| 3,774,616 | 11/1973 | White et al. | 128/200.26 |
| 3,946,742 | 3/1976 | Eross | 128/351 |
| 4,169,473 | 10/1979 | Samelson | 128/848 |
| 4,223,671 | 9/1980 | Muto | 128/200.26 |
| 4,270,529 | 6/1981 | Muto | 128/200 |
| 4,326,515 | 4/1982 | Shaffer et al. | 128/207 |
| 4,329,984 | 5/1982 | Kervin | 128/207 |
| 4,425,911 | 1/1984 | Luomanen et al. | 128/200.26 |
| 4,466,434 | 8/1984 | Brownstein | 128/200.26 X |
| 4,495,945 | 1/1985 | Liegner | 128/200 |
| 4,626,240 | 6/1987 | Gardy | 128/848 |
| 4,640,273 | 2/1987 | Greene et al. | 128/136 |
| 4,850,371 | 7/1989 | Broadhurst et al. | 128/719 |

FOREIGN PATENT DOCUMENTS 9003199 4/1990 World Int. Prop. O. ...... 128/200.26

Primary Examiner—Robert A. Hafer
Assistant Examiner—Sam Rimell
Attorney, Agent, or Firm—Eugene Chovanes

[57] ABSTRACT

A bite block to protect against a patient's biting into an instrument inserted through the mouth in a medical procedure. As a patient bites on the block against a sloping channel, the block is more firmly seated in the mouth, and the tongue is more firmly held depressed.

13 Claims, 3 Drawing Sheets

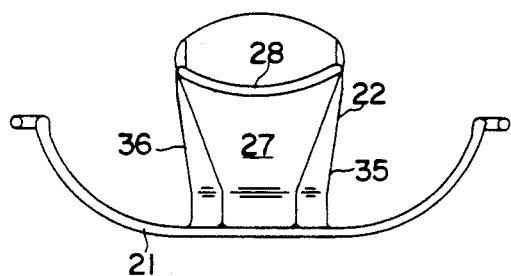
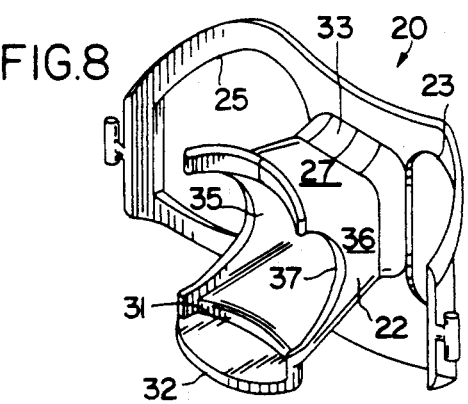
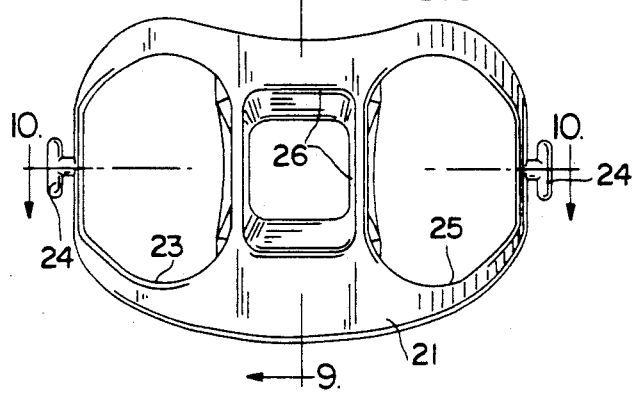
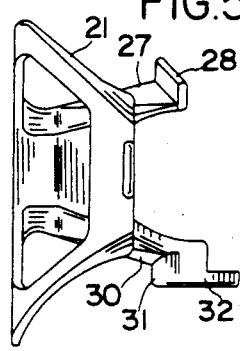
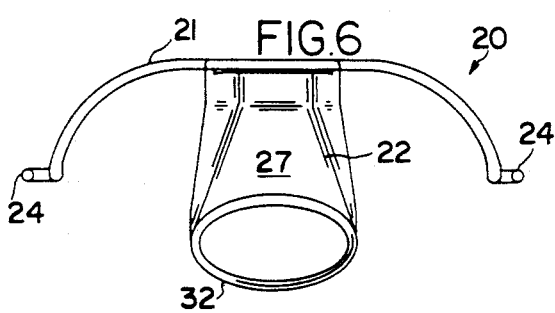
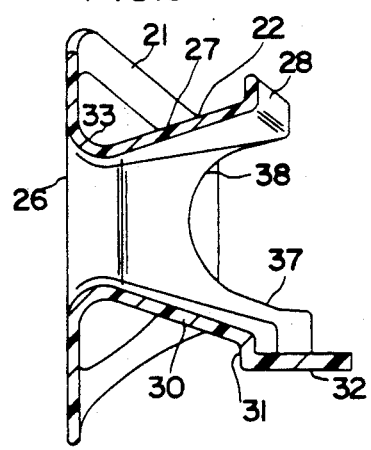
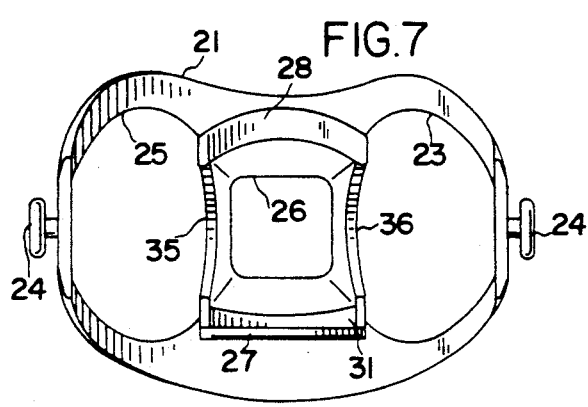

ENDOSCOPIC BITE BLOCK

BACKGROUND OF THE INVENTION

Instruments, such as endoscopes, are inserted through a person's mouth into the human body, in medical procedures. To prevent the patient from biting into the instrument, a bite block is used which is generally a plastic tube which is positioned in the patient's open mouth. The instrument is then inserted through the bite block opening into the stomach or other areas.

Having a flexible rod-like instrument inserted through the mouth, on through the throat into the alimentary canal is an unnatural and unpleasant sensation to the human body, and the body struggles, voluntarily and involuntarily, to eject or destroy the instrument, particularly when the person is partially sedated. The tongue attempts to push both the instrument and the bite block which is protecting the instrument out of the mouth; the teeth bite together to attempt to bite through. The lips also work to aid in the attempted expulsion and destruction. The function of the bite block is to oppose the body's actions and to protect the patient and instrument, and to permit the physician to insert the instrument with a minimum of trouble, and to carry out the medical procedure.

Prior art bite blocks, while in place in the mouth, generally work as intended but very often the struggling patient is successful in displacing them, particularly by vigorously working the tongue so as to push the bite block out of the mouth, even while the teeth are working to bite into the block and instrument. The teeth are then free to bite into the instrument. The mouth often assists in this ejection of the bite block by opening and closing about the bite block.

With persons who are particularly strong, the problem is even greater because of such strength.

SUMMARY OF THE PRESENT INVENTION

The bite block of the present invention uses the actions of a struggling patient to keep the bite block in place in the mouth, and to keep the lips, tongue, teeth and mouth all in proper position so that the physician can use the medical instrument with the greatest safety to not only the patient and instrument, but to the physician himself who often must place his finger into the mouth to guide the instrument.

When the patient chews on the block, sloping surfaces on a channel cause the bite block to move back into the mouth, where it seats firmly. A lip guard seats the front of the block firmly against the outside of the mouth against the lips. A tongue depressor, which firmly forces the tongue downward as the teeth compress against the upper and lower surfaces of the channel, keeps the tongue seated below the mouthguard, where it cannot struggle to push the block out of the mouth by flicking or otherwise. Finally, rear teeth guards create a barrier against the back of the teeth in the event the block does move forward in the patient's mouth, so that the block cannot be ejected out of the mouth, even if the mouth is opened wide. The block is arched high into the hard palate to firmly yet comfortably hold the mouth in a wide open position, giving the physician an optimum area of access for the instrument, while keeping the mouth, teeth, and jaws substantially immobilized.

In summary, the bite block of the invention becomes more firmly seated and the tongue more firmly held, the more a patient struggles or chews, while permitting the physician optimum access to the patient, not only with an instrument but also with the physician's fingers. The block keeps the mouth wide open and relatively immobilized.

DETAILED DESCRIPTION OF THE DRAWINGS

FIG. 1 is an isometric view of an endoscopic bite block as viewed from the front, showing certain details of construction and design, all in accordance with the invention. There is also shown in dot-and-dash outline a portion of an endoscopic tube inserted through the central aperture of the bite block and, in addition, the dot-and-dash profile of the first finger of the left hand within the lefthand port of the bite block, to assist in the proper deflection of the endoscopic tube.

FIG. 3 is a front elevational view of the endoscopic bite block.

FIG. 4 is a plan view of the bite block shown in FIG. 3.

FIG. 5 is a side elevational view (as viewed from the righthand side of FIG. 3).

FIG. 6 is a bottom plan view of the bite block shown in FIG. 3.

FIG. 7 is a rear elevational view of the bite block shown in FIG. 3.

FIG. 8 is an isometric view showing details of the bite block as viewed from the rear side (on a slightly reduced scale).

FIG. 9 is an enlarged sectional elevational view taken on the line 9,9 of FIG. 3.

DESCRIPTION OF THE PREFERRED EMBODIMENT

Figure 1:
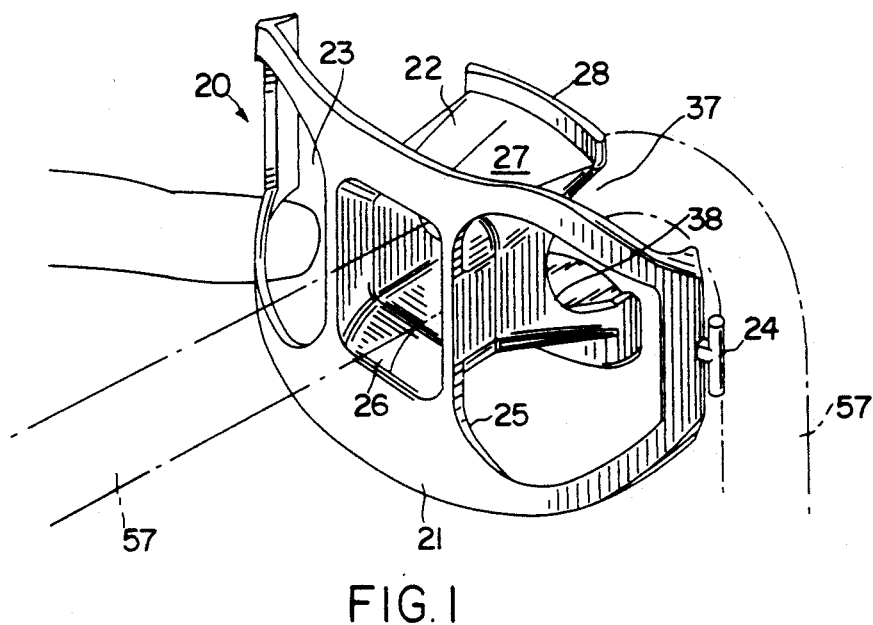

A bite block 20 is formed of a suitably molded plastic, with a thickness throughout of about 1/16" to 3/16", and has a front piece 21 and a rear channel 22 extending therefrom. Front piece 21 is intended to extend around the front of an open mouth over the lips. The front piece 21 has side openings or ports 23 and 25. At each side of front piece 21, anchors 24 are in T form and receive an elastic headband, not shown, that extends around the back of the head to hold the bite block in place. Holes in the headband provide adjustability. The T anchors 24 pass through selected holes, in the well known manner.

Of utmost importance to the invention is the shape of the channel 22. The channel 22 is integral with the front piece 21 and extends rearwardly therefrom. The front opening 26 is shown in rectangular form but may be elliptical or round, or other suitable shape, and is relatively large so that not only can the instrument be inserted readily in the opening 26, but the channel 22 requires the mouth of the patient to be wide open and in a relatively disadvantaged and immobilized position with respect to any subsequent efforts to dislodge the block by the patient, as will be seen from a later explanation of, particularly, FIG. 2B.

Channel 22 has a slightly curved upper surface 27 that rises upward rearwardly, and a vertically extending upper teeth guard 28 at the rear thereof, suitably curved to generally conform to the curve of the roof of the mouth. Channel 22 has at the bottom thereof a relatively flat declining lower surface 30 which has extending vertically downward at the rear thereof lower teeth guard 31. Integral with 31 and extending rearwardly horizontally therefrom is tongue depressor 32 in the form of a flat oval, preferably having a roughened lower surface. Channel 22 joins front piece 21 by means of an integral rounded, or fillet, segment 33.

The sides 35 and 36 of channel 22 are generally flat and slightly inclined outwardly from front to back. Each side has a substantial lateral opening or cut-out 37 having an arcuate contour 38 as seen in the drawings, and particularly FIG. 1, the ports 23 and 25 are large enough to permit the insertion of a surgeon's or nurse's finger or an auxilliary instrument or instruments, such as a suction tube, into the patient's mouth, and the arcuate lateral openings or cut-outs 37 are adapted to receive the tip of a finger and to aid in positioning or controlling the endoscopic tube or to pass an auxilliary instrument down the patient's throat.

Figure 2A:
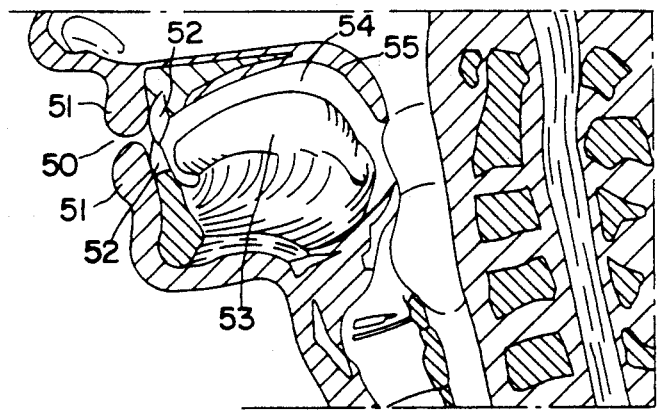
FIG. 2A is a semi-schematic fragmentary sectional elevational view of a human head, illustrating the anatomical parts involved in the use of the endoscopic bite block shown in FIG. 1.

FIG. 2A shows a patient before the bite block 20 of the invention is inserted. Mouth 50 is closed with lips 51 closed and teeth 52 touching. Tongue 53 extends within the mouth cavity 54 having palate 55 at the roof of the cavity.

Figure 2B:
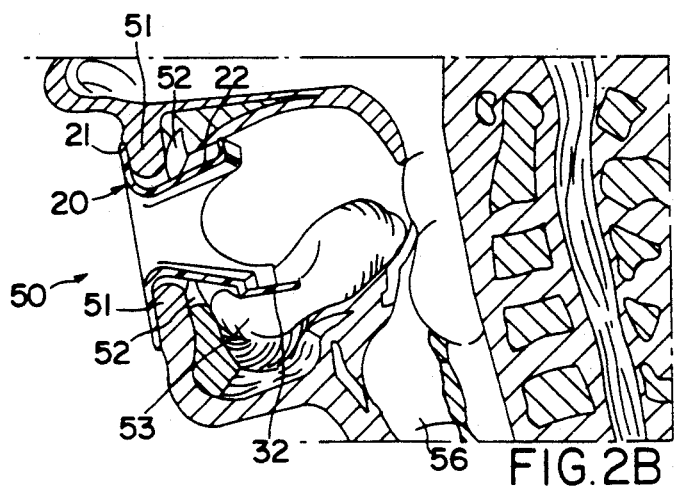
FIG. 2B is a front elevational view of the endoscopic bite block of the invention inserted within the oral cavity.
Figure 10:
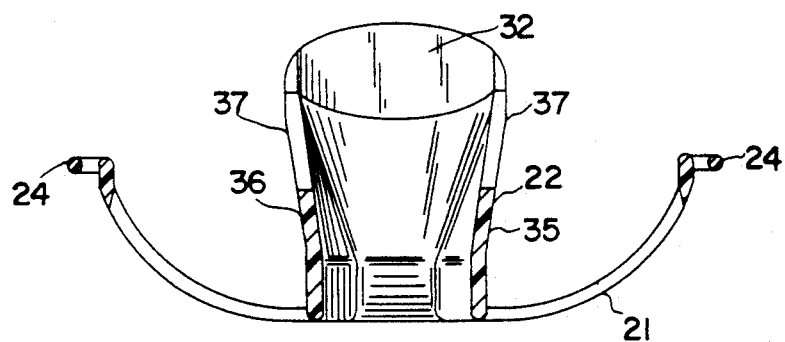
FIG. 10 is an enlarged sectional plan view taken on the line 10,10 of FIG. 3.

In use, the bite block 20 is positioned as shown in FIG. 2B. The mouth 50 is wide open and front piece 21 abuts the front of the face against the lips 51 which surround the channel 22 adjacent the inner surface of the front piece 21. Teeth 52 are in contact with the upper and lower surfaces 27 and 30 of the channel 22 and are exerting a biting effect on the channel 22. Tongue depressor 32 is forcing tongue 53 downwardly against the bottom jaw. It can be seen from FIG. 2B that a clear passageway in the patient extends through the mouth to the patient's throat 56, to accept the medical instrument, specifically an endoscope 57, as represented in phantom in FIG. 1.

Figure 11A:
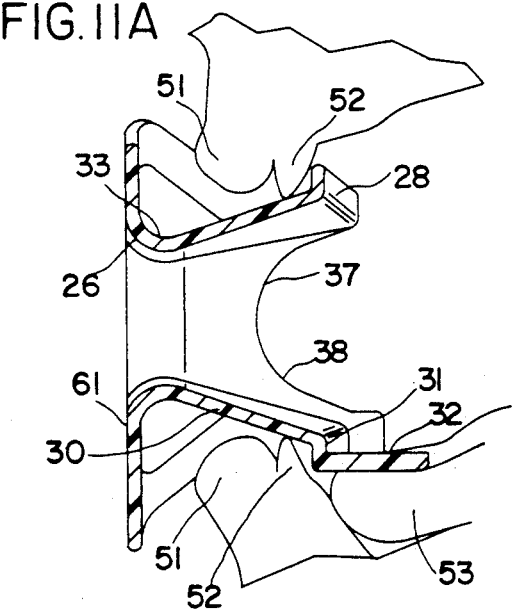
FIG. 11A is an enlarged sectional elevational view similar to FIG. 9, but showing the bite block in an initial positioning within the oral cavity, shown in fragmentary outline, prior to any biting action.
Figure 11B:
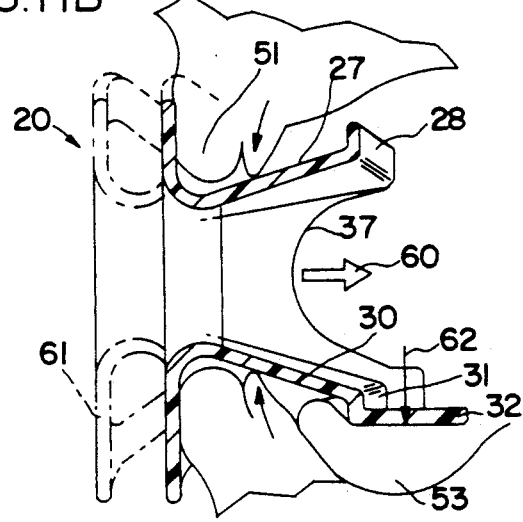
FIG. 11B is a view similar to FIG. 11A but showing how the biting action of the upper and lower incisors force the bite block forceably into the oral cavity and trap the tongue more securely.

The effects of the patient's biting on the bite block 20 is shown in FIGS. 11A and 11B. In 11A, the block is partially inserted into the mouth with the upper rear teeth guard 28 against the back of the upper teeth, and the lower rear teeth guard 31 against the back of the lower teeth. The tongue depressor 32 rests loosely against the top of the tongue 53.

In FIG. 11B, there are shown the effects of the teeth biting toward one another. The teeth slide down the upper and lower inclined surfaces 27 and 30, causing the block to move inwardly as shown by arrow 60 from the phantom position 61, which is the position of the block in FIG. 11A, to the position shown in solid lines in FIG. 11B. Further, the tongue depressor 32 moves downwardly, as shown by arrow 62, to force the tongue 53 downwardly against the lower jaw, where it is clamped and held securely so that it cannot, in the patient's struggle to eject the block, wiggle the tongue to a rearward position where it then can press up against the back of the block in an attempt to eject it from the mouth.

The inclined upper and lower surfaces 27 and 30 described above can be further described as a "slippery slope" wherein the teeth 52 slip down the slope of the upper and lower surfaces 27 and 30 of the channel 22 to firmly and securely position the bite block 20 in place, and hold the tongue 53 firmly in a depressed position.

Even if the patient does succeed in getting the block 20 forward, the rear teeth guards 28 and 31 prevent the block from being ejected beyond the teeth, whereby the teeth are free to bite into the instrument and/or the physician's fingers, if they are in the mouth. The block 20 is of such a height in the patient's mouth that the mouth is wide open when the block 20 is in place. The guard 28 is arched high into the hard palate. When positioning the block 20, the physician must maneuver the block 20 into position by possibly tilting the bite block 20 and stretching the mouth 50 to get the block in past the rear teeth guards 28 and 31. Since the patient's mouth is wide open and held in this position by the teeth guards 28 and 31, any straight-out ejection of the block is resisted by the teeth guards 28 and 31.

It is often necessary for the physician to insert a finger into the patient's mouth to assist in the procedure as seen in FIG. 1 in phantom. With the block 20 of the invention, the side openings or parts 23 and 25 permit a finger or fingers to be inserted from either side and readily into an opening or cut-out 37 in channel 22. The or-arcuate curved side 38 of opening or cut-out 37 permits the finger to have ready access to the instrument.

The wide front piece 21 keeps the block in place in the patient's mouth, even with patients without teeth.

I claim:

1. In an endoscopy bite block including a front piece to fit over a patient's mouth which has a central opening communicating with a channel member extending into the patient's mouth to receive and pass an endoscopic tube, the improvement comprising:
   said bite block having
   at least one port adjacent said central opening and channel member large enough to permit entry of a finger and/or auxilliary instrument means,
   said channel member having
   at least one lateral cut-out extending from an inner end of said channel member also to permit passage of a finger,
   whereby a finger may be inserted through said port past the inner end of said channel member to contact and control said endoscopic tube and/or an auxilliary instrument.

2. A bite block of claim 1 wherein said lateral cut-out opening adjacent the inner end of the channel member has an arcuate configuration.

3. A bite block of claim 2 wherein said channel member includes:
   slippery slope means including
   an upper surface of said channel member inclined upwardly and rearwardly and
   a lower surface of said channel member inclined downwardly and rearwardly
   whereby said slippery slope means act to force said bite block into the mouth under biting pressure.

4. A bite block of claim 3 also including
   at least one tooth guard means in conjunction with said channel member for contacting the back of a patient's teeth and inhibiting forward movement of said bite block, whereby said slippery slope means and said tooth guard means cooperate to prevent ejection of said bite block from the patient's mouth under in-use conditions.

5. A bite block of claim 4 comprising upper and lower tooth guard means.

6. A bite block of claim 5 wherein said upper tooth guard means is a substantial member extending vertically upward from said channel member and said lower tooth guard means is a substantial member extending vertically downward from said channel member.

7. A bite block of claim 6 also including tongue depressor means extending downwardly from said channel member.

8. A bite block of claim 7 wherein said tongue depressor means is integral with said lower tooth guard means.

9. A bite block of claim 8 wherein said tongue depressor means extends horizontally rearwardly from said lower tooth guard means and has a relatively flat lower surface for contacting the tongue.

10. A bite block of claim 9 wherein said tongue depressor means is oval and has a roughened lower surface.

11. In an endoscopy bite block including a front piece to fit over a patient's mouth which has a central opening communicating with a channel member extending into the patient's mouth to receive and pass an endoscopic tube, the improvement comprising said bite block having a pair of side ports, one on each side of and adjacent said central opening channel member, said side ports being large enough to permit a finger and/or auxilliary instrument means to be inserted past the inner end of said channel member, said channel member having a pair of lateral cut-out openings, one on each side, extending from an inner end of said channel member, said channel member having slippery slope means including an upper surface inclined upwardly and rearwardly and a lower surface inclined downwardly and rearwardly which surfaces act to force said bite block into the mouth under biting pressure, and substantial upper and lower tooth guard means extending vertically from said channel member to contact the back of a patient's teeth to inhibit forward movement of said bite block, whereby said slippery slope means and tooth guard means cooperate to prevent ejection of said bite block from the patient's mouth under in-use conditions.

12. A bite block of claim 11 having tongue depressor means extending downwardly from said channel member, and also cooperating to resist ejection of said bite block under in-use conditions.

13. A bite block of claim 10 wherein said tongue depressor means extends horizontally rearwardly from said lower tooth guard means and has a relatively flat lower surface for contacting the tongue.

* * * * *